United States Patent
Szakelyhidi, Jr. et al.

(10) Patent No.: US 7,753,913 B2
(45) Date of Patent: Jul. 13, 2010

(54) MAGNETIC TARGETING DEVICE

(75) Inventors: David C. Szakelyhidi, Jr., Harmony, PA (US); Alex V. Cardinali, Alexandria, VA (US); Joel D. Stitzel, Blacksburg, VA (US); Alfred A. Durham, Roanoke, VA (US); Alfred L. Wicks, Blacksburg, VA (US)

(73) Assignee: Virginia Polytechnic Institute and State University, Blacksburg, VA (US)

( * ) Notice: Subject to any disclaimer, the term of this patent is extended or adjusted under 35 U.S.C. 154(b) by 1627 days.

(21) Appl. No.: 10/679,166

(22) Filed: Oct. 3, 2003

(65) Prior Publication Data
US 2005/0075562 A1    Apr. 7, 2005

Related U.S. Application Data

(60) Provisional application No. 60/415,952, filed on Oct. 3, 2002.

(51) Int. Cl.
   *A61B 17/58* (2006.01)
(52) U.S. Cl. ........................................ 606/96
(58) Field of Classification Search ............... 128/899; 606/95–99
   See application file for complete search history.

(56) References Cited

U.S. PATENT DOCUMENTS

| 4,054,881 A | * | 10/1977 | Raab ..................... 342/448 |
| 4,103,683 A | | 8/1978 | Neufeld |
| 4,621,628 A | | 11/1986 | Brudermann |
| 4,622,644 A | * | 11/1986 | Hansen ..................... 702/153 |
| 4,622,959 A | | 11/1986 | Marcus |
| 4,625,718 A | | 12/1986 | Olerud et al. |
| 4,667,664 A | | 5/1987 | Taylor et al. |
| 4,733,654 A | | 3/1988 | Marino |

(Continued)

FOREIGN PATENT DOCUMENTS

EP    0 628 287 A    12/1994

(Continued)

OTHER PUBLICATIONS

*Semiconductor Sensors Data Handbook SC17*, Philips Electronics, Sep. 2000.

(Continued)

*Primary Examiner*—Thomas C Barrett
*Assistant Examiner*—Nicholas Woodall
(74) *Attorney, Agent, or Firm*—Charles S. Sara, Esq.; Dewitt Ross & Stevens S.C.

(57) ABSTRACT

A device and method for targeting objects and specifically for locating intramedullary screw openings is described. The device and method include a target magnet and a sensor comprising an elliptical array of magnetoresistive elements, designed to give information on the three-dimensional orientation of the magnet. The sensor array is designed such that each magnetoresistive element is a member of an opposing pair and relays information on their alignment with the target magnet. The array is connected to a display such that the position of the sensor in relation to the target magnet is easily discerned. The invention is lightweight and portable, capable of operating on batteries and can be used in primitive situations where a stable supply of electricity is not available.

50 Claims, 7 Drawing Sheets

U.S. PATENT DOCUMENTS

| | | | |
|---|---|---|---|
| 4,805,607 A | 2/1989 | Engelhardt et al. | |
| 4,817,591 A | 4/1989 | Klaue | |
| 4,846,162 A | 7/1989 | Moehring | |
| 4,848,327 A | 7/1989 | Perdue | |
| 4,881,535 A | 11/1989 | Sohngen | |
| 4,911,153 A | 3/1990 | Border | |
| 4,913,137 A | 4/1990 | Azer et al. | |
| 5,034,013 A | 7/1991 | Kyle et al. | |
| 5,047,034 A | 9/1991 | Sohngen | |
| 5,049,151 A | 9/1991 | Durham et al. | |
| 5,127,913 A | 7/1992 | Thomas | |
| 5,167,663 A | 12/1992 | Brumfield | |
| 5,178,621 A | 1/1993 | Cook et al. | |
| 5,251,127 A | 10/1993 | Raab | |
| 5,305,203 A | 4/1994 | Raab | |
| 5,334,192 A | 8/1994 | Behrens | |
| 5,411,503 A | 5/1995 | Hollstien et al. | |
| 5,417,688 A | 5/1995 | Elstrom et al. | |
| 5,425,382 A * | 6/1995 | Golden et al. | 128/899 |
| 5,433,720 A | 7/1995 | Faccioli et al. | |
| 5,458,602 A | 10/1995 | Goble et al. | |
| 5,472,444 A | 12/1995 | Huebner et al. | |
| 5,489,284 A | 2/1996 | James et al. | |
| 5,514,145 A | 5/1996 | Durham et al. | |
| 5,540,691 A | 7/1996 | Elstrom et al. | |
| 5,562,667 A | 10/1996 | Shuler et al. | |
| 5,584,838 A * | 12/1996 | Rona et al. | 606/96 |
| 5,611,353 A | 3/1997 | Dance et al. | |
| 5,617,857 A | 4/1997 | Chader et al. | |
| 5,658,287 A | 8/1997 | Hofmann et al. | |
| 5,707,375 A | 1/1998 | Durham et al. | |
| 5,728,128 A | 3/1998 | Crickenberger et al. | |
| 5,731,996 A * | 3/1998 | Gilbert | 702/150 |
| 5,748,767 A | 5/1998 | Raab | |
| 5,779,705 A | 7/1998 | Matthews | |
| 5,879,352 A | 3/1999 | Filoso et al. | |
| 5,891,158 A | 4/1999 | Manwaring et al. | |
| 5,935,127 A | 8/1999 | Border | |
| 5,951,561 A | 9/1999 | Pepper et al. | |
| 5,957,847 A | 9/1999 | Minakuchi et al. | |
| 5,987,960 A | 11/1999 | Messner et al. | |
| 6,036,696 A | 3/2000 | Lambrecht et al. | |
| 6,039,739 A | 3/2000 | Simon | |
| 6,039,742 A | 3/2000 | Krettek et al. | |
| 6,074,394 A | 6/2000 | Krause | |
| 6,081,741 A | 6/2000 | Hollis | |
| 6,093,192 A | 7/2000 | Abel | |
| 6,106,528 A | 8/2000 | Durham et al. | |
| 6,126,661 A * | 10/2000 | Faccioli et al. | 606/64 |
| 6,129,729 A | 10/2000 | Snyder | |
| 6,162,228 A | 12/2000 | Durham | |
| 6,168,595 B1 | 1/2001 | Durham et al. | |
| 6,183,477 B1 | 2/2001 | Pepper | |
| 6,200,316 B1 | 3/2001 | Zwirkoski et al. | |
| 6,205,411 B1 | 3/2001 | DiGioia, III et al. | |
| 6,214,013 B1 | 4/2001 | Lambrecht et al. | |
| 6,216,028 B1 * | 4/2001 | Haynor et al. | 600/424 |
| 6,296,645 B1 | 10/2001 | Hover et al. | |
| 6,309,396 B1 | 10/2001 | Ritland | |
| 6,443,954 B1 | 9/2002 | Bramlet et al. | |
| 6,503,249 B1 | 1/2003 | Krause | |
| 6,517,541 B1 | 2/2003 | Sesic | |
| 6,562,042 B2 | 5/2003 | Nelson | |
| 6,895,266 B1 * | 5/2005 | Hollis | 600/407 |
| 2002/0029041 A1 | 3/2002 | Hover et al. | |
| 2002/0045900 A1 | 4/2002 | Harder et al. | |
| 2002/0133172 A1 | 9/2002 | Lambrecht et al. | |
| 2002/0151897 A1 | 10/2002 | Zirkle, Jr. | |
| 2002/0161369 A1 | 10/2002 | Bramlet et al. | |
| 2002/0173792 A1 | 11/2002 | Severns et al. | |
| 2003/0069581 A1 | 4/2003 | Stinson et al. | |
| 2005/0080427 A1 * | 4/2005 | Govari et al. | 606/98 |

FOREIGN PATENT DOCUMENTS

| | | |
|---|---|---|
| WO | WO 97/13467 A | 4/1997 |

OTHER PUBLICATIONS (1999) 20th Century Orthopaedics. *The American Academy of Orthopaedic Surgeons* 47.

(2001) Femur fracture care frequent cause of lawsuit. *American Academy of Orthopaedic Surgeons* 49.

Catamo, L., Rotini, R., Rocca, M., Giardino, R., and Fontanesi, G. (1998) Distal centering in locked intramedullary osteosynthesis of the femur: use of a magnet-resistant probe. *Chir Organi Mov* 83, 375-379.

Conn, K.S. and Hallett, J.P. (1998), A simple laser guide to reduce the screening time during the insertion of dynamic hip screws, *Injury* 29, 539-541.

Durham, A.A. and Crickenberger, D.P. (1998) Magnetic Distal Targeting for Modular Intramedullary Nails, *Techniques in Orthopaedics* 13, 71-78.

Garcia-Lopez, A., Marco, F., and Lopez-Duran, L. (1998) Unreamed intramedullary locking nailing for open tibial fractures, *Int. Orthop.* 22, 97-101.

Hems, T.E.J.. and Bhullar, T.P. (1996), Interlocking nailing of humeral shaft fractures: the Oxford experience 1991 to 1994, *Injury* 27, 485-489.

Karachalios, T., Babis, G., Tsarouchas, J., Sapkas, G., and Pantazopoulos, T. (2000) The clinical performance of a small diameter tibial nailing system with a mechanical distal aiming device. *International Journal of the Care of the Injured* 31, 451-459.

Kelley, S.S., Bonar, S., Hussamy, O.D., and Morrison, J.A. (1995) A simple technique for insertion of distal screws into interlocking nails. *J.Orthop.Trauma* 9, 227-230.

Knothe, U., Knothe Tate, M.L., Klaue, K., and Perren, S.M. (2000) Development of a new self-locking intramedullary nail system: Testing of handling aspects and mechanical properties, *International Journal of the Care of the Injured* 31, 617-626.

Krettek, C., Konemann, B., Mannss, J., Schandelmaier, P., Schmidt, U., and Tscherne, H. (1996) [Analysis of implantation-induced nail deformation and roentgen morphometric studies as the principle for an aiming device for distal interlocking nailing without roentgen image intensification]. *Unfallchirurg* 99, 671-678.

Krettek.C., Konemann,B., Miclau,T., Schlandermaier,P., and Blauth,M. (1997) in vitro and in vivo radiomorphic analyses of distal screw hole position of the solid tibial nail following insertion. *Clinical Biomechanics* 12, 198-200.

Krettek, C., Konemann, B., Miclau, T., Kolbli, R., Machreich, T., Kromm, A., and Tscherne, H. (1998) A new mechanical aiming device for the placement of distal interlocking screws in femoral nails. *Arch Orthop.Trauma Surg* 117, 147-152.

Krettek, C., Konemann, B., Farouk, O., Miclau, T., Kromm, A., and Tscherne, H. (1998) Experimental study of distal interlocking of a solid tibial nail: radiation-independent distal aiming device (DAD) versus freehand technique (FHT), *J. Orthop.* Trauma 12, 373-378.

Larsen, S.E., Nielsen, K.S., Larsen, M.S., and Kristensen, S.S. (2000) Treatment of femoral shaft fractures with Grosse-Kempf intramedullary nail, *Journal of Orthopaedic Science* 5, 328-332.

Lepore, S., Capuano, N., Lepore, L., and Romano, G. (2000) Preliminary clinical and radiographic results with the Fixion intramedullary nail: an inflatable self-locking system for long bone fractures, Journal of Orthopaedic Traumatology 3, 135-140.

Mahaisavariya, B., Laupattarakasem, W., and Kosuwon, W. (1992) An aiming device for distal locking in closed locked femoral nailing. *Injury* 23, 143-144.

Markmiller, M., Tjarksen, M., Mayr, E., and Ruter, A. (2000) The unreamed tibia nail: Multicenter study of the AO/ASIF, Langbecker's Arch Surg 385, 276-283.

Pennig, D., Oppenheim, W., Faccioli, G., and Rossi, S. (1997) Intramedullary locked nailing of femur and tibia: Insertion of distal locking screws without image intensifier. *Injury* 28, 323-326.

Pispati, V.G. and Reddy, M.R. (1995), Complications in tibial interlocking nailing.

Slomczykowski, M.A., Hofstetter, R., Sati, M., Krettek, C., and Nolte, L.P. (2001) Novel computer-assisted fluoroscopy system for intraoperative guidance: feasibility study for distal locking of femoral nails. *J.Orthop.Trauma* 15, 122-131.

Tyropoulos, S. and Garnavos, C. (2001) A new distal targeting device for closed interlocking nailing. *International Journal of the Care of the Injured* 32, 732-735.

Viant, W.J., Phillips, R., Griffiths, J.G., Ozanian, T.O., Mohsen, A.M., Cain, T.J., Karpinski, M.R., and Sherman, K.P. (1997) A computer assisted orthopaedic surgical system for distal locking of intramedullary nails. *Proc.Inst.Mech.Eng* [H.] 211, 293-300.

Walcher, F., Frank, J., and Marzi, I. (2000), Retrograde Nailing of Distal Femoral Fracture-Clear and Potential Indications, *European Journal of Trauma* 26, 155-168.

Waldron, V.D. (2000), Targeting device for pinning finger fractures, Am.J.Orthop. 29, 733.

Zacheja, J., Bach, T., and Clasbrummel, B. (2000) Application of Microsensors for Minimally Invasive Vascular Flow Measurements and Fracture Repair Systems., Hanover, Germany.

Orthomatrix® Magellan I.M. Nail System, 2 pages.

http://www.medmedia.com, Wheeless' Textbook of Orthopaedics, Synthes IM Femoral Nail Insertion Technique, 2 pages.

http://www.medmedia.com, Wheeless' Textbook of Orthopaedics, Femoral . . . , 3 pages.

http://www.medmedia.com, Wheeless' Textbook of Orthopaedics, Proximal Inter-Locking for Synthes Nail, 2 pages.

http://www.biometmerck.com, Femoral Nails, Total Solution for Trauma, ST-Pro Femoral Nailing System, 3 pages brochure.

http://www.medmedia.com, Wheeless' Textbook of Orthopaedics, Distal Inter-Locking, 3 pages.

Krettek, C., et al. (1996), [Development and initial clinical use of an aiming device for distal boring in interlocking nailing without roentgen image intensifier for the unreamed tibial nail], *Unfallchirurg* 99, 845-854.

Krettek, C., et al. (1997), [A comparison of a fluoroscopy-free mechanical targeting system and a free-hand technic for the placement of distal interlocking screws of tibial nails], *Chirurg* 68, 1194-1201.

Krettek, C., et al. (1998), [Comparison of a radiation-independent aiming system and free-hand technique for distal locking of unslotted femoral nails], *Unfallchirurg* 101, 822-829.

Phillips, R., et al.(1993), "Steps towards computer assisted locking of intramedullary nails", *IEEE*.

Rappold, G., et al. (2001), "Implant of the Proximal Femoral Nail", *European Journal of Trauma* 27, 333-337.

\* cited by examiner

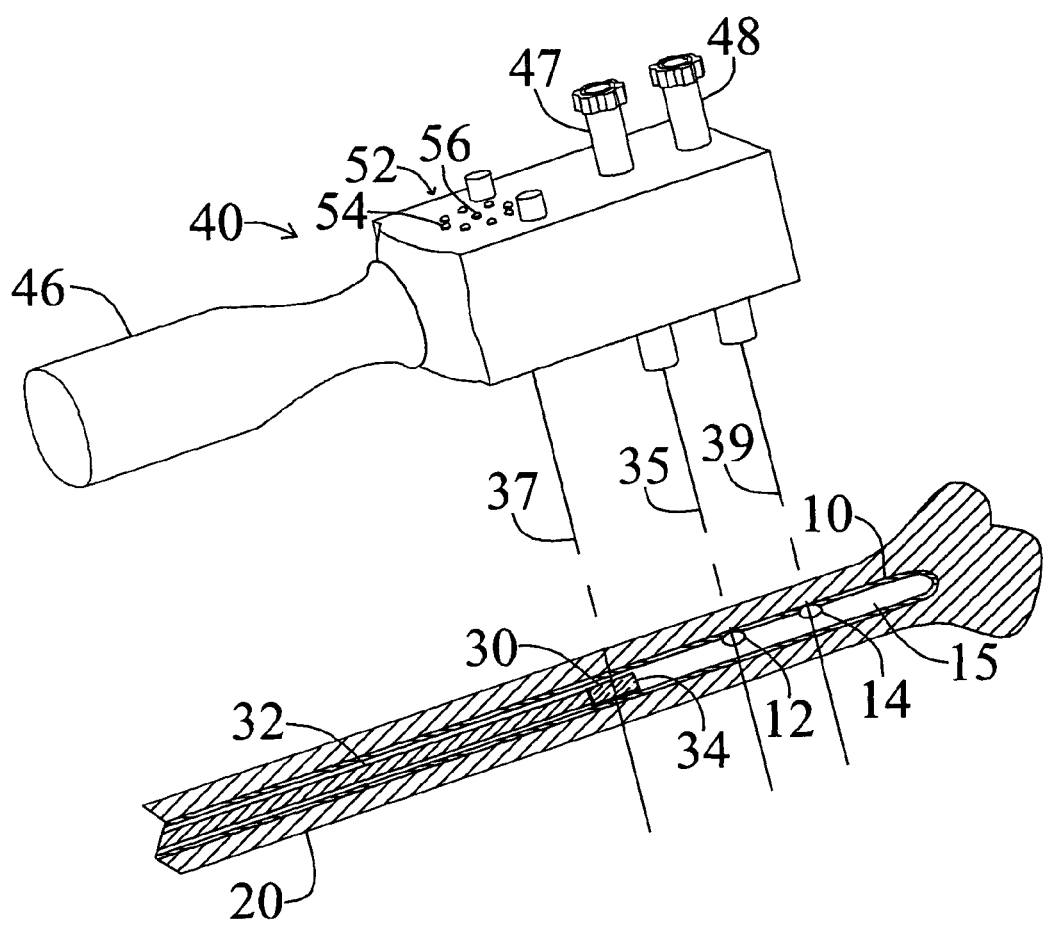
FIG. 1
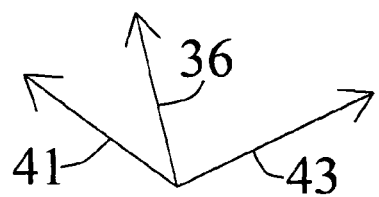

MAGNETIC TARGETING DEVICE

CROSS REFERENCE TO RELATED APPLICATIONS

This application claims priority under 35 USC §119(e) to U.S. Provisional Patent Application 60/415,952 filed Oct. 3, 2002, the entirety of which is incorporated herein by reference.

REFERENCE TO CITATIONS

Complete bibliographical citations to the references can be found in the list preceding the claims.

FIELD OF THE INVENTION

The present invention relates to a targeting device in general and specifically to a method and device for positioning locking screws for intramedullary nails. The invention describes sensitive methods for magnetic detection of transverse interlocking screw openings in real time.

DESCRIPTION OF THE PRIOR ART

Each year, approximately 14,000 femoral and 12,000 tibial internal fracture repairs are performed by orthopedic surgeons in the United States. Internal fixation of long bones has allowed shorter hospitalization times and earlier weight bearing for the patient, compared to plaster cast or external fixation.

The medical procedure involves the fixation of long-bone fractures by inserting an intramedullary nail ("IMN"), also known as a locking rod, a long, thin-walled, metallic nail, into the medullary canal of the damaged bone. The surgeon introduces the implant by creating an opening in the proximal end of the bone, exposing the medullary canal. The bone fragments are aligned, and the IMN is passed through the fragments, creating a means for internal support.

The IMN is prefabricated with openings in the proximal and distal ends, which are designed to accept transverse interlocking screws. These screws are essential to control the rotation and translation of the bone fragments with respect to each other. To insert the transverse, interlocking screws, it is necessary to align and drill through the bone to meet the proximal and distal interlocking screw openings of the IMN.

One of the most difficult parts of intramedullary nailing of long bones is locating and drilling the interlocking screw openings. IMN interlocking screw placement requires the surgeon to locate the openings in the nail, center the drill and advance the bit through the bone to meet them. The interlocking screws are then inserted. Proximal interlocking screw placement is relatively easy because the openings can be located with an external guide attached to the end of the IMN. However, this technique does not work well for distal interlocking screw placement.

Complicating the process of identifying and drilling the distal interlocking screw openings is the deformation that routinely occurs to the IMN upon implantation in the medullary canal. Studies have shown that deformation occurs in several planes due to medial-lateral and anterior-posterior flexion of the distal nail after it has been inserted (Krettek et al., 1996; 1997; 1998). On insertion, the distal IMN may exhibit a mean lateral deflection of 4.5±3.0 mm and dorsal deflection of 7.8±5.8 mm. In addition, rotational deformation of the distal IMN has been measured at 0.3±0.7 degrees. The distal nail may deform from its original shape in any of these coordinates to some degree. The nail can deform to the shape of the medullary canal upon insertion. The shape of the canal varies widely from person to person, and it is not possible to predict how the nail will deform accordingly. Therefore, it is difficult to determine what the resultant location of the distal interlocking openings will be relative to their initial position.

In addition, there are narrow tolerances between the screw and interlocking opening. To avoid any complications, it is important to place the interlocking screws accurately. The physical tolerance between the screw opening and screw must be taken into account when targeting and drilling to allow room for proper insertion.

If the drill bit is not within the tolerance constraints or misses the opening, a second attempt must be made. Unfortunately, once a hole in the bone is started, it is difficult to correct. In some cases, the bone may be too weak to accommodate another hole, and then bone grafting or other means of fracture fixation must be employed.

Prior Art X-Ray Technology

One prior art method for providing a precise location of the transverse distal openings in IMN's uses X-rays. Correct alignment is indicated when the desired interlocking opening appears as a perfect circle under X-ray fluoroscopy with the drill bit in the exact center. If alignment is lost, the drilling must be stopped and the drill bit realigned using further X-ray imaging. In its most rudimentary form the opening is drilled with freehand means. The process of drill bit centering requires the soft tissue of the patient's extremity to be separated all the way to the bone so the surgeon has sufficient room to maneuver. X-ray imaging requires long periods of X-ray exposure first, to identify the location of the transverse distal opening and second, to correctly drill the opening. Thus, X-ray exposure may accumulate to dangerous levels for both the surgeon and patient. In addition, X-ray imaging necessitates moving X-ray equipment into and out of position, allowing numerous opportunities for loss of alignment each time the equipment is repositioned.

The need to reduce damage to soft tissue during these procedures has led to the use of less invasive techniques. These techniques include percutaneous methods wherein surgical instruments are inserted through small incisions in the skin, thus reducing soft tissue damage. Methods to optimize percutaneous techniques include aiming devices, which rely on mechanical approaches to locate the distal screw openings.

The simplest of these mechanical devices uses an external arm with openings that correspond to the screw opening location in the IMN. Once the IMN is implanted, the external guide arm is attached firmly to its proximal end creating a solid link. The openings corresponding to the screw openings then serve as a drill sleeve for drill alignment. Unfortunately, due to the tight tolerances required for screw location and the degree of distal nail deformation occurring, this approach still requires an inordinate amount of X-ray exposure and still carries the risk of misplacing the opening. Further, while methods to limit exposure of individual patients to X-rays have been explored, the need to perform the surgery using X-rays for detection means that the surgical team is serially subjected to X-ray exposure.

Prior Art Magnetic Technology

The desire to target accurately without X-ray imaging has led to recent attempts to use magnets for targeting of the distal IMN screw openings. Devices have been developed that use external magnetic sensors to find the position of a flux field induced in the IMN by permanent magnets or electromagnets (U.S. Pat. No. 4,621,628 to Brudermann). Some devices have even tried to magnetize the whole IMN and look for variations in the magnetic flux that occur around the interlocking openings (Zacheja et al., 2000).

Other devices target on a magnet placed inside the IMN at the same position as the opening. For instance, U.S. Pat. Nos. 5,049,151, 5,514,145 and 5,703,375 to Durham et al. teach the use of a pivotable magnetic targeting device to position a guide wire by which a cannulated drill is directed to align the drill bit with the interlocking screw opening. The targeting device is a second, pivoting magnet, attached to a drill sleeve acting as a compass to direct the drill bit toward the target magnet. The Durham et al. device uses a magnet placed inside the IMN, directly aligned with the axis of the distal screw opening to be targeted. The magnet is inserted on a rod through the proximal opening in the hollow nail, while its insertion depth is fixed by a locking pin. Once the magnet is placed adjacent, generally proximal to the distal openings, a skin incision is marked using a magnetic compass to locate the position of the internal magnet which projects central flux lines parallel to the axis of the opening. After the skin and tissue are separated to allow working room, another magnet on a central pivot inside a tube is inserted down to the bone surface. These two magnets attract each other and align a guide wire, which is then inserted in the bone surface. The magnets are removed and a cannulated drill bit is advanced over the guide wire, which is now aligned directly with the axis of the opening. Finally the interlocking screw is inserted and the procedure is repeated for the more proximal opening.

Advantages of Magnetic Targeting

Magnetic targeting has some significant advantages. Magnetic fields can penetrate the IMN and human tissue without being distorted or causing physiologic damage, unlike X-rays. Also, magnetic devices can be to require little power, allowing portable, battery operation.

Disadvantages of Prior Art Magnetic Targeting

A notable drawback is that most targeting devices are manufactured to work only with specific nails and are not adaptable to others. In addition, the magnetic field must be powerful enough to be detectable at distances of 10 cm. This is the average maximum distance encountered between the center of the IMN and the exterior of the patient's limb at the thickest site of IMN implantation, usually about the femur. While electro-magnets can generate stronger fields, devices that use electric current inside the body to create magnetic fields require stringent FDA approval because of their inherent danger.

U.S. Pat. No. 4,621,628 to Brudermann describes a method for the magnetic identification of transverse locking openings wherein the sensor is inserted into the IMN and the magnet is placed percutaneously on the broken limb. In this disclosure the sensors, in the form of intersecting Hall elements, are inserted into the IMN to the area of the transverse screw opening and are connected to an external display. The magnet is placed on the surface of the skin until the axis of the field is aligned, wherein a zero point indication is signaled on the display. While Brudermann teaches a non X-ray means of detecting the transverse screw opening, it suffers from the draw backs of inserting an electrical device inside the medullary cavity, the low sensitivity of the Hall Effect sensors used to detect the magnets, the lack of three-dimensional resolution to the display and the lack of portability to the entire device.

In a more recent use of magnetic targeting, U.S. Pat. No. 6,162,228, to Durham describes a method of using a target magnet inserted into the IMN and a target sensor, which is essentially mechanical, having a compass that indicates the position of the target magnet in the IMN. This invention is similar to the other Durham patents identified above with the exception that the target magnet produces an output comprising a light or buzzer when the targeting unit is aligned. While this device solves the problem of excessive exposure to X-rays, it has neither the sensitivity to penetrate the combined tissue layers nor the ability to discriminate the orientation of the screw opening in three-dimensional space. It does allow real time feedback while drilling because the target magnet occupies a space offset from the internal diameter of the screw opening during targeting.

Due to the aforementioned problems with locating the distal screw openings of IMNs, including excessive X-ray exposure, excessive soft tissue damage, the need for expensive and bulky equipment and the desire for real time imaging, there is a need for a sensitive and easily visualized sensing device that is both portable and safe for use in locating distal transverse screw openings in IMNs.

SUMMARY OF THE INVENTION

The present invention provides a method and device for percutaneously locating transverse screw openings in IMNs using a magnetic target and a sensitive and accurate targeting device.

Specifically, the invention is directed to a targeting device for detecting a precise location and position within a hollow object having an opening, comprising a magnet adapted to be positioned within the opening of the tube for providing a directional field, wherein the magnet includes a three-dimensional orientation on an x-axis, a y-axis and a z-axis; and a target device, including sensing means for identifying the magnet location along the three-dimensional orientation of the magnet; and a display means, wherein the display means represents the orientation of the sensing means.

The present invention is also directed to a method for detecting a precise location and position within a hollow object having an opening and an external surface, comprising inserting and positioning a magnet having a three-dimensional orientation in the opening of the object at a discrete position in the tube, wherein the magnet includes a three-dimensional orientation on an x-axis, a y-axis and a z-axis; providing a target device external to the discrete position, wherein the targeting device comprises sensing means for identifying the magnet location and position along the three-dimensional orientation of the magnet and a display means indicating the position of the sensing means in relation to the magnet; and moving the target device along the external surface location until the sensing means senses the three-dimensional orientation of the magnet.

The present invention is further directed to a targeting device for percutaneously detecting the location and position of screw openings within an intramedullary nail for the internal fixation of long bones, wherein the intramedullary nail has a longitudinal opening and screw openings, comprising a magnet adapted to be positioned within the longitudinal opening of the intramedullary nail for providing a directional field, wherein the magnet includes a three-dimensional orientation on an x-axis, a y-axis and a z-axis; and a target device, including sensing means for identifying the magnet location along the three-dimensional orientation of the magnet; and a display means, wherein the display means represents the orientation of the sensing means.

The present invention is still further directed to a method for detecting the location and position of interlocking transverse screw openings within an intramedullary nail for the internal fixation of long bones, wherein the intramedullary nail includes a longitudinal opening and interlocking screw openings, comprising inserting and positioning a magnet having a three-dimensional orientation in the opening of the intramedullary nail to a discrete position proximal to the transverse interlocking screw opening; providing a targeting device external to the discrete position, wherein the targeting device comprises sensing means for identifying the magnet location along the three-dimensional orientation of the magnet and a display means indicating the position of the sensing means in relation to the magnet; and moving the target device along the external surface location until the sensing means senses the three-dimensional orientation of the magnet.

The present invention also provides a target magnet that can be affixed to the end of an insertion rod and inserted in the cavity of an IMN to a discrete position proximal to the transverse interlocking screw opening. The magnet has an axisymmetric flux field thereby relating information on its orientation in relation to the screw opening. In addition, the method is designed such that the flux field is detectable at a distance of 10 cm or more. Ten cm is the average maximum distance encountered between the intramedullary canal and the outside of the patient's limb.

The invention further describes a method for sensing the flux field whereby commercially available magneto-resistive (MR) elements are arranged in an elliptical pattern thereby being aligned perpendicular to the lines of flux. The targeting device comprises a sensor comprised of eight MR elements arrayed in an elliptical pattern with the elements comprising four pairs opposing member elements. Because direct centering of the target between members of a pair of MR sensors elicits the same magnitude response from each member of the pair, the difference in output between pair members is relative to the spatial difference of each pair member from the target magnet. By comparing voltage offset between opposing sensors in the array, it can be determined which direction in the field the sensors must be moved to elicit an equivalent output, thus indicating exact centering over the target magnet.

The targeting device locates a permanent magnet locked in place offset from the openings to be drilled. The north pole of the magnet must face medially (along the z-axis) so that it projects a magnetic field having a central line of flux parallel to the axis of the interlocking opening. From outside the extremity in which the IMN is inserted, the targeting is performed by an array of magnetic sensors held parallel to the medial plane. These sensors are embedded in a targeting device handle which has at least one and preferably two drill sleeves attached at its distal end. The surgeon can advance the drill bit through the bone without hitting the magnet, while maintaining alignment feedback in real time. A display on the handle of the targeting device includes a position indicator, preferably in the form of a "bull's-eye" of light emitting diodes (LED's). The outside of the display will consist of a ring of lights, with one offsetting light in the center. The ring of lights to indicate the position the drill sleeve must move to have correct alignment. When properly aligned, the ring of lights will be off and the central light will be lit. The surgeon is then ready to advance the drill bit through the drill sleeve and drill a hole in the bone in order to insert the interlocking screws without aid of fluoroscopy or extraneous targeting systems.

In a further embodiment of the invention, the sensor display comprises a handle with the display in the middle and a drill sleeve in the distal end. By this means, the sensor can be aligned with the target magnet and the interlocking drill opening drilled while simultaneously, in real time, monitoring the position of the drill bit in relation to the interlocking screw opening.

It is another aspect of the invention that the target magnet is designed to relay information about its position and orientation in relation to the axis of the transverse interlocking screw opening. Thus, the magnet is designed to have a non-circular, axisymmetric flux field allowing the sensor to distinguish rotation about the z-axis, while the peak flux lines perpendicular from the magnet indicate its exact center.

Advantages:

Advantageously, the system of the present invention can use some of the existing magnet insertion techniques, but applies an electronic approach to the targeting issue. The targeting device of the present invention locates a permanent magnet that will be locked in place offset from the opening to be drilled.

The present invention makes a significant contribution to orthopedic surgeries involving IMN interlocking. Approximately 30,000 of these surgeries are performed each year, providing a larger market for the device. The present invention has advantages that alleviate many problems that arise during IMN distal interlocking screw opening identification.

The advantages of the present invention include: portability, low power requirement; X-ray independent identification, targeting independent of IMN deformation, providing a non-invasive/non-radioactive imaging technique, accurate and repeatable identification of the distal IMN, adaptability for use with existing IMN's, ease of learning and ease of use, and simple design and concomitant inexpensive means of manufacture. In addition, there are no in vivo active or passive electronics; no x-ray imaging is needed for targeting; there is real time feedback of alignment; and the system is battery operable.

The magnetic targeting device can improve orthopedic surgeons' ability to target and drill distal IMN interlocking screw openings. The device has significant advantages that will appeal to orthopedic surgeons that perform IMN insertions and interlocking.

This device is able to resolve all degrees of freedom needed to accurately align the drill bit with the central axis of the interlocking opening, within the given tolerances. This device gives feedback of position in real time, so that alignment can be maintained during drilling. The prototype device achieves targeting without x-ray exposure. Although fluoroscopy may be employed to check proper screw interlocking, this device has the potential to eliminate x-ray use during targeting.

The application of this prototype allows for a percutaneous approach to interlocking screw opening targeting and drilling. Also, it can be used to locate the exact location of skin incisions needed above the interlocking openings for insertion of the drill bit. A visual positioning display was created to provide feedback of drill alignment during targeting. It is also possible to provide configure the prototype to provide audible and tactile feedback as well. The prototype includes a calibration circuit used to zero the sensors prior to targeting. This calibration can negate the effects of extraneous magnetic field present in the operating room.

This device has additional benefits. The prototype's target magnet could be adaptable to any nail, providing the nail is hollow and non-ferrous. The cylindrical magnet shape, with a diameter preferably less than 3 millimeters ("mm"), allows the magnet to be placed lengthwise in the smallest, hollow IMN's used for bones such as the humorous or tibia. The device has low power requirements and can be powered by battery. The prototype can be incorporated with existing drill sleeves, IMN's, and magnet insertion rods, while only needing a handle to be fabricated to connect all the pieces.

Other Uses of Invention:

While the preferred embodiment of this invention will be described with respect to the use of an IMN for repairing long bones, such as femurs, it is within the scope of the present invention to have other uses. These include: tracking and positioning of medical instruments, including endoscopes, catheters and implants within the body; use of location and targeting devices used in industry, particularly with materials that are X-ray sensitive; replacement of jigs and other measurement systems used in industry and manufacturing; providing positioning feedback for robotic devices; and, any process requiring blind hole targeting in non ferrous materials including, precise positioning of opposing elements such as in cabinetry making, fiberglass fabrication and construction and processes involving ceramic and tile fabrication and installation. As previously discussed, the use of electromagnets is not recommended for in-vivo uses; however, electromagnets may be well suited to these other uses of the invention.

The objects and advantages of the invention will appear more fully from the following detailed description of the preferred embodiment of the invention made in conjunction with the accompanying drawings.

BRIEF DESCRIPTION OF THE DRAWINGS

FIG. 1 is a perspective view of the invention illustrating the target magnet inserted in the IMN and attached to an insertion rod with the target sensing device connected to a drill sleeve.

DETAILED DESCRIPTION OF THE INVENTION

Figure 2:
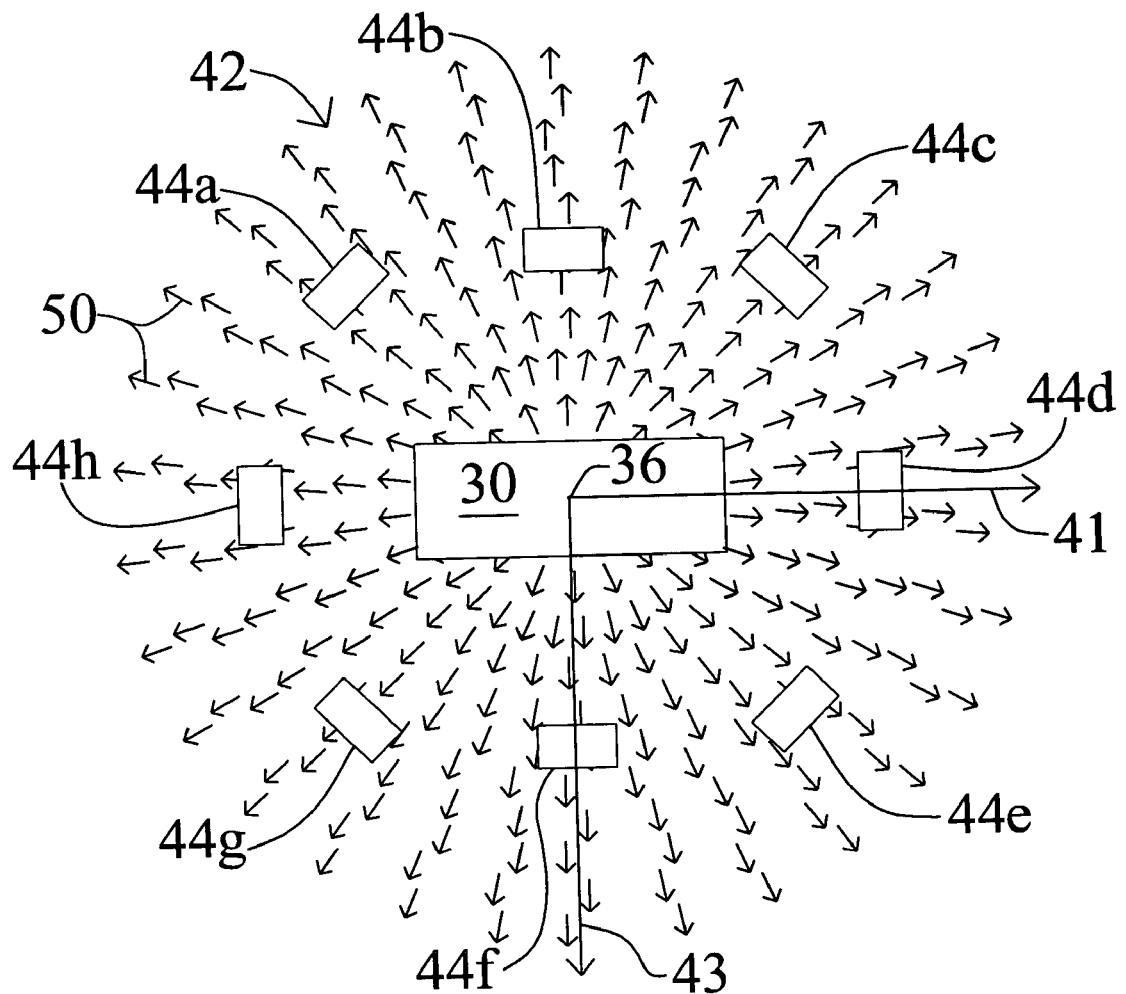
FIG. 2 is a representation of the flux lines produced by the magnet. The elliptical array is shown in which each sensor lies perpendicular to the flux field. This arrangement allows for equivalent voltage outputs from all the sensors when the array is centered in the flux field over the magnet.

As embodied and broadly described herein, the present invention is directed to a method and device for detecting the position of interlocking transverse screw openings within an IMN for the internal fixation of long bones. The IMN device consists of electronics which interface to magnetic sensors and a display to indicate target proximity. The housing supports the electronics and a drill sleeve. The unit is typically powered by a battery.

Intramedullary Nail

Referring now to FIG. 1, there is illustrated a hollow intramedullary nail (IMN) 10, known to the art. Examples of IMN's are prevalent in the prior art. For example, reference is made to U.S. Pat. No. 6,503,249 to Krause and the patents to Durham (cited herein), the contents of which are incorporated herein by reference for a description of IMN's and manners of use. The IMN 10 is an elongated metal rod having a hollow body portion or shaft 15. The IMN 10 includes a first locking screw opening 12 and a second more distal locking screw opening 14. While the screw openings 12, 14 of typical IMNs 10 are transverse, i.e., positioned at a ninety degree angle in relation to the nail as illustrated in FIG. 1, it is within the scope of the present invention to have non-transverse screw openings, i.e., openings at other than ninety degrees in relation to the length of the IMN 10. For purposes of this disclosure such openings are termed "oblique." Prior to placement of the IMN 10, a reaming rod known to the art is worked through the medullary cavity of a long bone 20, such as a broken femur, tibia or humerus bone. The IMN 10 is then placed within the medullary cavity for securing within the bone 20 by means of cross-locking screws or bolts positioned through the screw openings 12, 14 (not illustrated in FIG. 1).

Magnet 30

In order to align and advance the drill bit (60 in FIG. 7) through the bone 20 accurately, the surgeon must have accurate knowledge of the position of the drill sleeves 47, 48 in relation to the axes 35, 39 of the transverse locking screw openings 12, 14. This requires a target magnet that provides a suitable magnetic field to resolve all degrees of freedom. Therefore, the magnetic field within the IMN 10 must have a shape and polarity that affords unique targeting information in all possible planes. For targeting with this approach, the flux lines 50, illustrated in FIG. 2, have a peak and a non-circular field shape about the axis of each plane so that the targeting sensors 44 may be aligned. A non-circular, axisymmetric field was selected; allowing the sensors 44 to distinguish rotation about the z-axis 36, while the peak flux lines 50 perpendicular from the magnet 30 indicate its exact center.

In verification of this design, Ansoft's Maxwell 3 D magnetic modeling program (http://www.ansoft.com/products.com/max3d) was used to compare various magnet shapes and orientations. The magnetic field that was found to afford the required properties for targeting would have a peak and a non-circular field shape about the axis of each plane so that the targeting sensors may distinguish position from any direction. The shape and polarity that was found to afford the optimal field was a cylindrical Neodymium Iron Boron (NdFeB) magnet that is polarized across its axis. A preferred size for the magnet has a diameter of about 3 mm and a length of about 7 mm. The field from this magnet must be detectable at a maximum distance typically encountered between the center of the IMN 10 and the outside of the patient's limb, which is approximately 10 centimeters ("cm"). For the small percentage of large patients who have an IMN place in an extremity of exceptional diameter, the surrounding tissue can be compressed to bring the distance below 10 cm.

It is within the scope of the present invention to use different magnet shapes and materials can be used as long as the sensor array used to target them is adjusted to match the flux field of the magnet. It must also provide the desired flux field for feedback of discriminate targeting in all required planes. Additionally, an electro-magnet may be used to achieve a similar field if desired.

Referring back to FIG. 1, a target magnet 30, attached to a magnet insertion rod 32 or other like device, is inserted into the IMN 10 in a specified orientation to a locking point 34 at the most distal transverse locking screw opening 14. A reaming rod, known to the art for conducting such a procedure, can be adapted for use as a magnet insertion rod 32. The adaptation would require a means for attaching the target magnet 30 to the distal end of the rod 32, with provisions for maintaining correct depth, rotation, and centering of the magnet 30 within the IMN 10. It is also within the scope of the present invention to eliminate the insertion rod 32 and provide an IMN 10 with a permanent magnet 30 mounted within the longitudinal open shaft 15 of the IMN 10. In this manner the IMN 10 would be formed with a previously mounted magnet 30 situated within the shaft 15 of the IMN 10 at the locking point 34.

The magnet 30 is designed to be axisymmetric with non-circular flux lines. The north pole of the magnet 30 must face medially (along the z-axis 36) so that it projects a magnetic field having a central line 37 of flux parallel to the axes 35, 39 of the interlocking screw openings 12, 14. Designed in this manner, the flux field 50 (shown in FIG. 2) of the magnet 30 relates information about its three-dimensional orientation along the x-axis 41, the y-axis 43, and the z-axis 36.

Magneto-resistive Sensors 44

As illustrated in FIG. 1, a targeting device 40 is then applied percutaneously to the approximate region of the interlocking screw openings 12, 14. In the embodiment illustrated, the targeting device 40 includes at least one pair of sensors and preferably a sensor array 42, described more fully below, and a handle 46. Located at the distal end of the targeting device 40 are drill sleeves 47, 48 situated within channels 47a and 48a (illustrated in FIG. 7). It is known to the art that drill sleeves 47, 48 are slibably positioned within channels 47a, 48a. In this manner, the sleeves 47, 48 can be slidably positioned directed on the bone 20 after an incision is made in the skin for accurate drilling.

Figure 4:
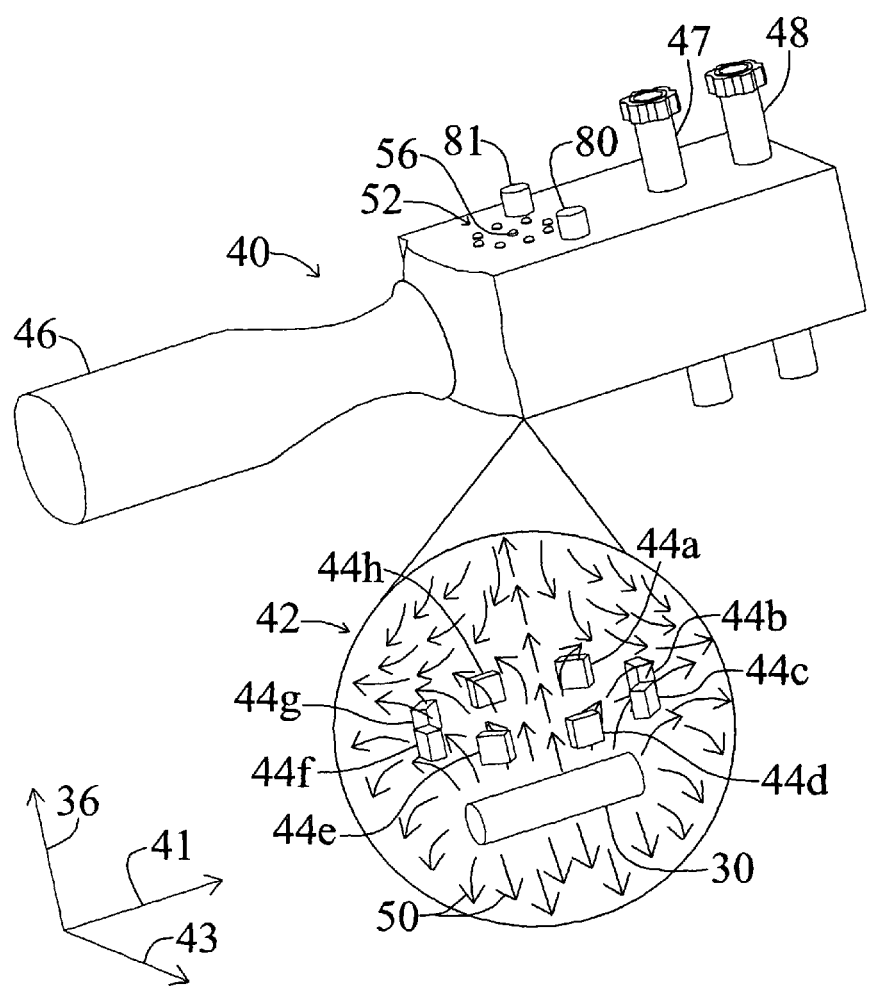
FIG. 4 is a schematic diagram of the sensing device with an insert representing the target magnet and flux lines and the elliptical sensing array in three-dimensional space.

Referring to FIGS. 1, 2 and 4, the sensor array 42 relates to sensors 44, which are designed to detect the magnetic flux lines 50 of the target magnet 30 and can be aligned to precisely identify the magnet 30 location. The target sensors 44 are designed to have a sufficient sensitivity and resolution to operate at a range of approximately 10 cm from the magnet 30. The field strength of the target magnet 30 at this distance will be below 1 Gauss, which is close to the value of the Earth's magnetic field. Therefore, a sensor 44 is needed that can sense very small changes in magnetic field. Sufficient resolution is gained by using a sensor 44 that has a sensitivity range of −2 to +2 Gauss. Such components are commercially available. For example, Phillips Semiconductors (Sunnyvale, Calif.) currently makes a MR field sensor that requires only 120 milliwatts of power, which is appropriate for battery powered operation (Phillips Semiconductors KMZ10B). The KMZ10B is comprised of a Wheatstone bridge arrangement of MR elements. The resistance of the MR elements changes in proportion to the orientation and strength of an external magnetic field in opposition to its own internal magnetization. Magnetic field measurements are obtained by supplying a voltage to the KMZ10B and then reading the differential voltages across the bridge. This output voltage is proportional to the angle and magnitude of the magnetic field and is sensitive over a field strength range of +/−2 kA/m. The field strength of the target magnet, at the maximum 10 cm, distance falls into this range. These sensors produce a maximum output when flux lines are perpendicular to its sensitive axis, +Hy.

The sensitivity of the KMZ10B is 20 millivolts per kA/m when supplied with 5 volts. The targeting circuitry allows the sensor outputs to be zeroed so that they only represent the magnitude of flux lines emitted from the target magnet. This allows compensation for extraneous fields from other sources in the operating room. Such extraneous sources could be the surgical drill, video monitors, lighting, and even the Earth's magnetic field. In addition, these sensors can provide sensing feedback for small variations of magnetic fields such as those present at a distance of 10 cm from the target magnet. The KMZ10B sensors have a sensitivity of 10 millivolts change per Gauss. They can also be nulled so that their outputs only represent changes in the flux lines emitted from the target magnet, thus allowing extraneous fields from other sources in the operating room to be ignored. Further, the KMZ10B sensors are extremely versatile; being very robust, able to withstand extremes in temperature, chemical challenges as well as having a low energy requirement. Further, these sensors can be configured in an array so that their collective outputs may be used for targeting.

It is within the scope of the present invention to utilize one sensor 44 in the invention. However, greater accuracy can be achieved by utilizing two or more sensors 44 preferably in pairs. In its preferred embodiment the array 42 of sensors includes eight MR sensors 44a-h in an elliptical array forming four pairs (44a-e, 44b-f, 44c-g, and 44d-h). Each sensor 44 in a pair opposes the other member of the pair. Each sensor 44 produces a maximum output when flux lines 50 are perpendicular to its sensitive side. This allows the angle and magnitude of the detected field to be known. As illustrated in FIG. 2, the elliptical arrangement of the sensors 44 allows them to be geometrically aligned with flux lines 50 of the target magnet 30. Each individual sensor 44 is oriented perpendicularly to the flux lines 50 that project radially outward from the target magnet 30, while being centered about the peak flux lines emitted along the z-axis 36, as illustrated in FIG. 2. This arrangement guarantees that each sensor 44 in the array 42 will be excited by the same magnitude and angle of flux when perfectly centered about the z-axis 36 of the magnet 30, and will produce the same output voltage.

Feedback for alignment is obtained by comparing the output voltages of opposing sensors pairs 44a-e, 44b-f, 44c-g, 44d-h within the array 42. It can be seen that if one sensor 44 in the pair is further from the target magnet 30, it will be exposed to a smaller field, showing a voltage imbalance, indicating misalignment. A visual display is used to indicate direction for correct alignment based on these voltage outputs. The same principle applies if a sensor pair 44a-e, 44b-f, 44c-g, 44d-h is rotated from correct alignment about an axis, where outputs will not be equivalent unless the angle of the flux seen by the sensor pairs is equal and opposite.

Figure 3A:
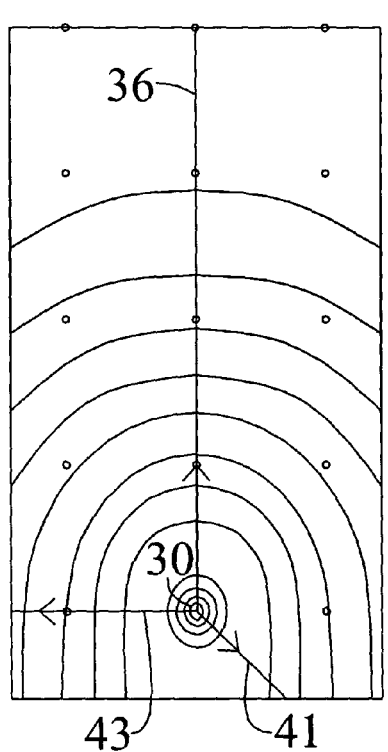
FIGS. 3a and 3b are graphs illustrating plots of flux density in the y-z and x-z planes above the chosen cylindrical magnet. The peak is centered exactly over the magnet, parallel with the z-axis and is detectable at the required targeting distance of 10 cm.
Figure 3B:
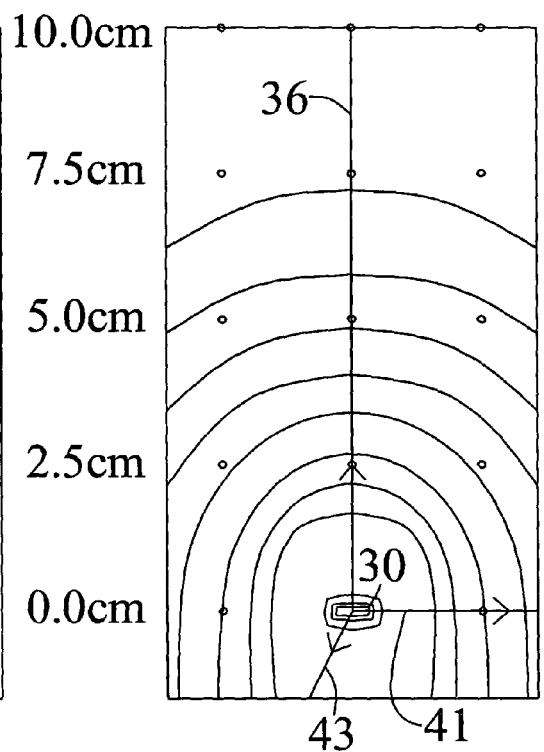

A plot of the flux lines in the x-y plane is illustrated in FIGS. 3a and 3b, which shows flux densities above the magnet 30, as well as orientation of the magnet polarity. It can be seen that there is a definitive peak that remains parallel to the z-axis 36 regardless of distance. This is important because the targeting device 30 and corresponding drill sleeves 47, 48 must remain parallel to the openings 12, 14 at all depths.

Arrangement of Sensors 44

The arrangement of the preferred embodiment of sensor pairs 44a-e, 44b-f, 44c-g, 44d-h so described allows each sensor 44 in the array to be excited by the same magnitude and angle of flux 50 when centered about the z-axis 36 of the magnet 30, and will produce the exact output voltage. The sensor array 42 can move in a plane perpendicular to the z-axis 36 and retain the same feedback of position because the field shape in that plane remains constant. The reading and accuracy of the target device 40 becomes stronger as the sensors 44 move closer to the target magnet 30, as best illustrated in FIG. 2 which shows the results of computer modeling of these flux lines in the x-y plane along with the optimal placement of the sensors 44.

Because the sensors 44 are aligned in opposing pair members, centering each pair over the target magnet 30 elicits the same magnitude output from each member of the pair. Upon exact centering, one member will "cancel out" the other member. Any deviation from exact center, in either rotation or translation, will cause an offset in opposing members of the sensor pair.

By comparing voltage offset between opposing sensors in the array 42, the direction in the field can be determined. Reference is made to FIG. 4 for a schematic of a preferred embodiment, in which the inset represents the sensor array 42 relative to the flux lines 50 generated by the magnet 30 (illustrated in FIG. 1). As described, the targeting device 40 allows centering with feedback of offset in the x-y plane, while providing feedback of rotation about x, y, and z axes 41, 43 and 36. Further, modifications to the present display can allow distinct, absolute and differential measurements of distance and rotation in separate axis (x, y and z), output to the user. Because the magnetic flux lines 50 lie in three dimensions, the target device 40 comprises a multi-axis targeting device. Further, the disclosed configuration of the target device 40 can compensate for constant, uniform (DC) magnetic fields that exist in the operating room, e.g., earth's magnetic field, lights, and instruments, but it is recommended that the operating table and other fixtures within an effective radius of the targeting magnet be non-ferrous. This compensation is possible because the targeting circuitry uses a differential measurement between sensors pairs, so as to affectively cancel any extraneous fields which would provide equal but opposite outputs.

Using the sensor array output, continuous feedback is provided for the surgeon to center the drill 60 (illustrated in FIG. 7) in each of the drill sleeves 47, 48 above the interlocking openings 12, 14 in the medial plane. The targeting electronics, known to the art, are used to compare opposing sensor outputs and determine their location within the magnetic field, drive a display 52 that indicates this position and performs calibration of the sensors 44. An example of circuitry which can be adapted to the present invention can be found in *Semiconductor Sensors Data Handbook SC*17, Philips Electronics, September 2000. It will be appreciated that the sensitivity of the targeting device 40 to movement is almost infinitely adjustable via the electronics.

The sensors 44 in the sensor array 42 should be sensitive to small changes in magnetic field, thereby making it possible to determine the position of the magnet 30 in the field with a resolution of less than a millimeter in translation and less than one degree of rotation. Calibration is necessary because each sensor 44 has an inherent offset at zero field due to manufacturing tolerances. Additionally, it is necessary to null any extraneous fields present in the operating room. Circuitry, known to the art, is provided that zeros the output of each sensor 44 so that the array 42 is ready for targeting. Calibration must be done with the sensors 44 away from any strong magnetic field, including that of the target magnet 30, so that the reading is not biased.

Once calibrated, it is possible to use the sensor array 42 to provide positioning data. When the array 42 is centered exactly over the target magnet 30 in the medial plane, all sensors 44a-h will have equal voltage outputs. Any deviation from exact center, in either rotation or translation, will cause an offset in opposing members of the sensor pair. By comparing voltage offset between opposing sensors in the array, the direction of the sensor in the field can be determined until the opposing sensors have equivalent outputs. Those having skill in the art will appreciate that the sensor array 42 must correspond to the magnetic field shape of the magnet 30 to allow feedback of position about the desired axis for a specific application. It will also be appreciated that for any specific application, the magnet size and material may be changed, as long as the correct magnetic field shape is maintained.

Readable Display 52

In a more preferred embodiment, illustrated in FIGS. 1 and 4, the outputs from the sensor array 42 are converted into a readable display 52 allowing the surgeon to precisely determine the location of the screw opening 14. In this example, the display 52 resembles a "bulls-eye" of light emitting diodes (LEDs) comprising a ring of colored lights 54a-h around a central "bulls eye" light 56 of another color. For example, the ring of lights 54a-h could be a yellow color and the central light 56 could be an offsetting color such as red. Each LED is tied to the corresponding sensor 44a-h in the elliptic array. If a sensor pair has a voltage difference between them, it will be indicated on the LED display 54a-h (illustrated in FIG. 5). An illuminated light means that the targeting device 40 must be moved in the direction of the light. The position indicating LEDs have a variable brightness, which decreases as the targeting device 40 moves toward correct alignment. When all target sensors 44a-h are properly aligned, each sensor 44 cancels the output of its opposite pair member, all lights 54a-h shut off and the central light 56 is illuminated. The lit central light 56 indicates correct placement of the drill sleeves 47, 48 for drilling the hole through the bone 20 and for correct placement of the transverse interlocking screws in the IMN interlocking screw openings 12, 14. In a further embodiment, it is well within the scope of the present invention to substitute the visual display described above with audible, tactile, or other feedback mechanisms to indicate alignment. Such mechanisms are well-known to the art.

Electronics

Figure 5:
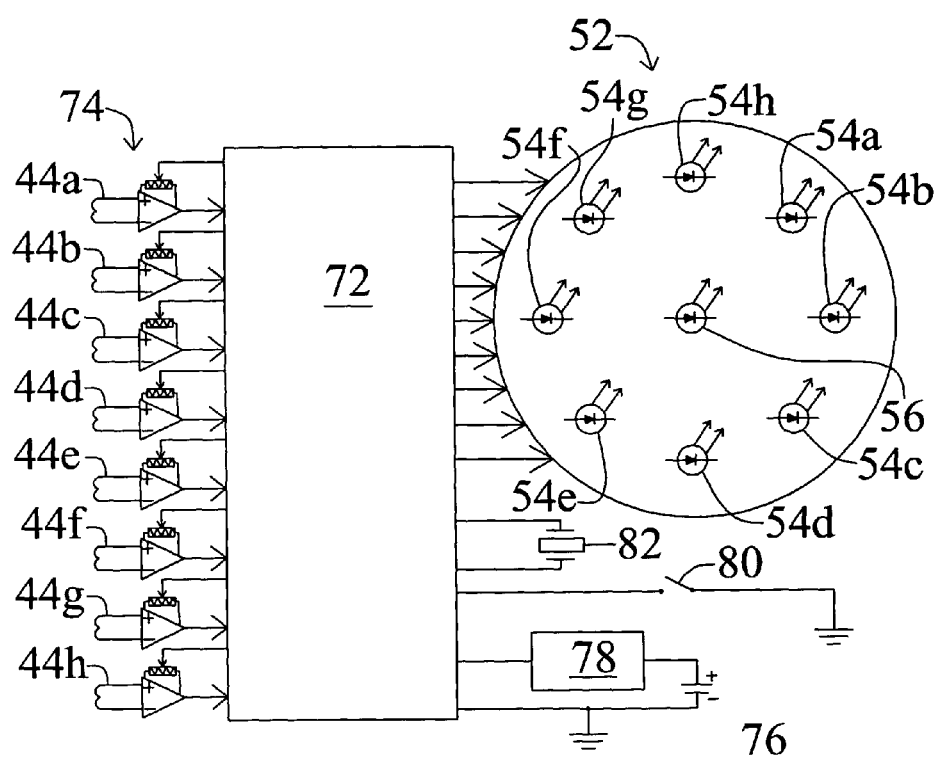
FIG. 5 is a diagrammatic illustration of the electronic system of the present invention.
Figure 6:
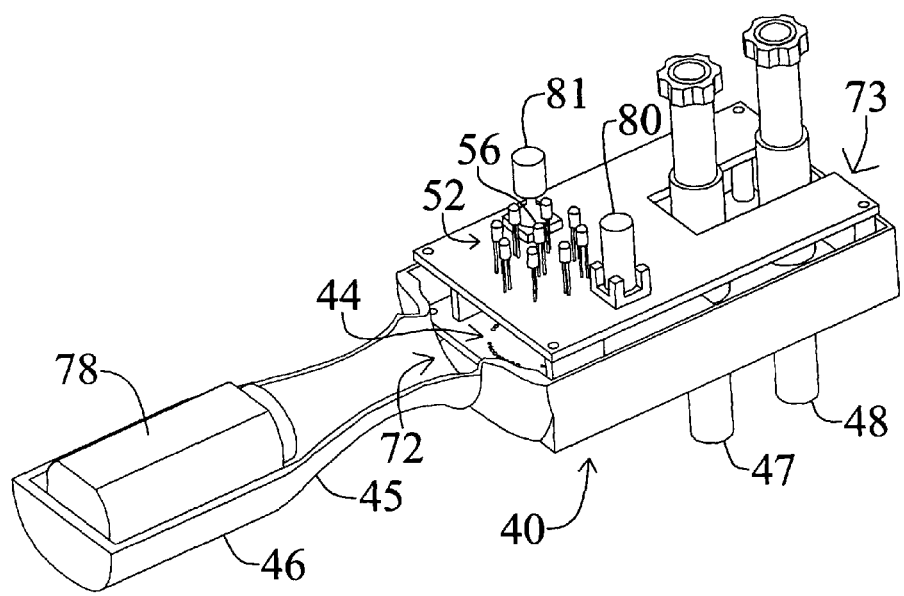
FIG. 6 is partially exploded perspective view of the targeting device illustrating the placement of the electronic system in the device.

The electronics perform the functions of acquiring and conditioning signals from the sensors 44, processing these signals, and driving the display 52. Reference is made to FIG. 5, which illustrates the system hardware block diagram generally referenced at 70 and FIG. 6 which illustrates the targeting device 40 without half of its casing 45. Within the system 70, there is a microcontroller 72 which is the heart of this system. The microcontroller 72 includes an on-board analog-to-digital converter (not shown) which is used to digitize signals from the instrumentation amplifiers 74. The instrumentation amplifiers 74 interface directly to the sensors 44. Computations are performed by the microcontroller 72 to determine which, if any of the display lights 54 should be illuminated in the sensor array 42.

Microcontrollers are known to the art. A representative example of a microcontroller is the Microchip PIC16F877 microcontroller (Microchip Technology Inc., Chandler, Ariz.). The Microchip PIC16F877 has the required 8 analog-to-digital converter inputs and enough outputs to drive an LED display, while still having left over ports for additional tasks in future revisions to the device. There are many benefits to using digital control. It uses less power, less area, and is lower cost than the analog components that would be required to perform the same functions. The microcontroller-based approach also allows easy adjustment of feedback sensitivity and other parameters during prototyping. These adjustments can be made by simply changing software, rather than having to change circuit components and hardware. The printed circuit board 73 will have a small connector that will allow a wired interface to the microcontroller to facilitate in-circuit programming.

There are several steps involved in using the microcontroller 72 for converting the sensor outputs into a visual display of alignment. The first task is to read the analog voltage inputs from the sensors 44 and convert them to digital format. A calibration mode can be entered by activating the calibration switch. This will put the software in a loop which cycles thru each analog-to-digital converter channel and records the offset present in each sensor 44 when held in a null field. These offset values are saved and then later subtracted from their respective channel values when in normal targeting mode, effectively canceling any extraneous fields or tolerance differences between sensors 44.

When in normal targeting mode, after the input is calibrated, the microcontroller 72 performs a comparison of sensor pair outputs 44A-E, 44B-F, 44C-G, and 44D-H. The input of each sensor 44 in a pair is subtracted to determine which one falls in a higher flux field. If one of the sensors 44 in a pair indicates a higher flux field, another software loop will light the appropriate LED 52 on the microcontroller's 72 output port, which indicates the desired direction for correct alignment. When all sensor pairs read voltages that are close in value, below a predetermined threshold, only the central LED 56 on the output port will be lit. At any time, the targeting device 40 can be removed from the field of the target magnet 30 and recalibrated if needed.

Each of the eight sensors 44A-H is supplied with an excitation of energy preferably from a battery 76 and generally about 5 volts. The differential output of each sensor 44 is fed into a signal conditioning instrumentation amplifier 74 in the microcontroller 72. Signal conditioning instrumentation amplifiers 74 are known to the art. A representative example of such an amplifier is identified as AD623 (Analog Devices, Norwood, Mass.). The amplifier 74 amplifies and shifts the sensor output signal to a level usable by the analog-to-digital converter of the microcontroller 72.

Power for the targeting device 40 is typically derived from a 9 volt battery 76 which runs through a voltage regulator 78 that provides a constant 5 volt supply for the system. Each component is set to operate at this voltage. The main power switch 80 (on/off) disconnects the battery, minimizing battery drain during storage. The switch 80 or a calibration switch 81 is used to put the device into calibration mode. The circuitry includes a crystal oscillator 82 used as a clock reference for the microcontroller 72. Connected to the output ports 84 of the microcontroller 72 is the sensor array 42, which includes low-current light emitting diodes 52 for visual positioning feedback of the sensors 44. Computations are performed by the microcontroller 72 to determine which, if any, of the LED's 52 should be illuminated.

Method of Use

Figure 7:
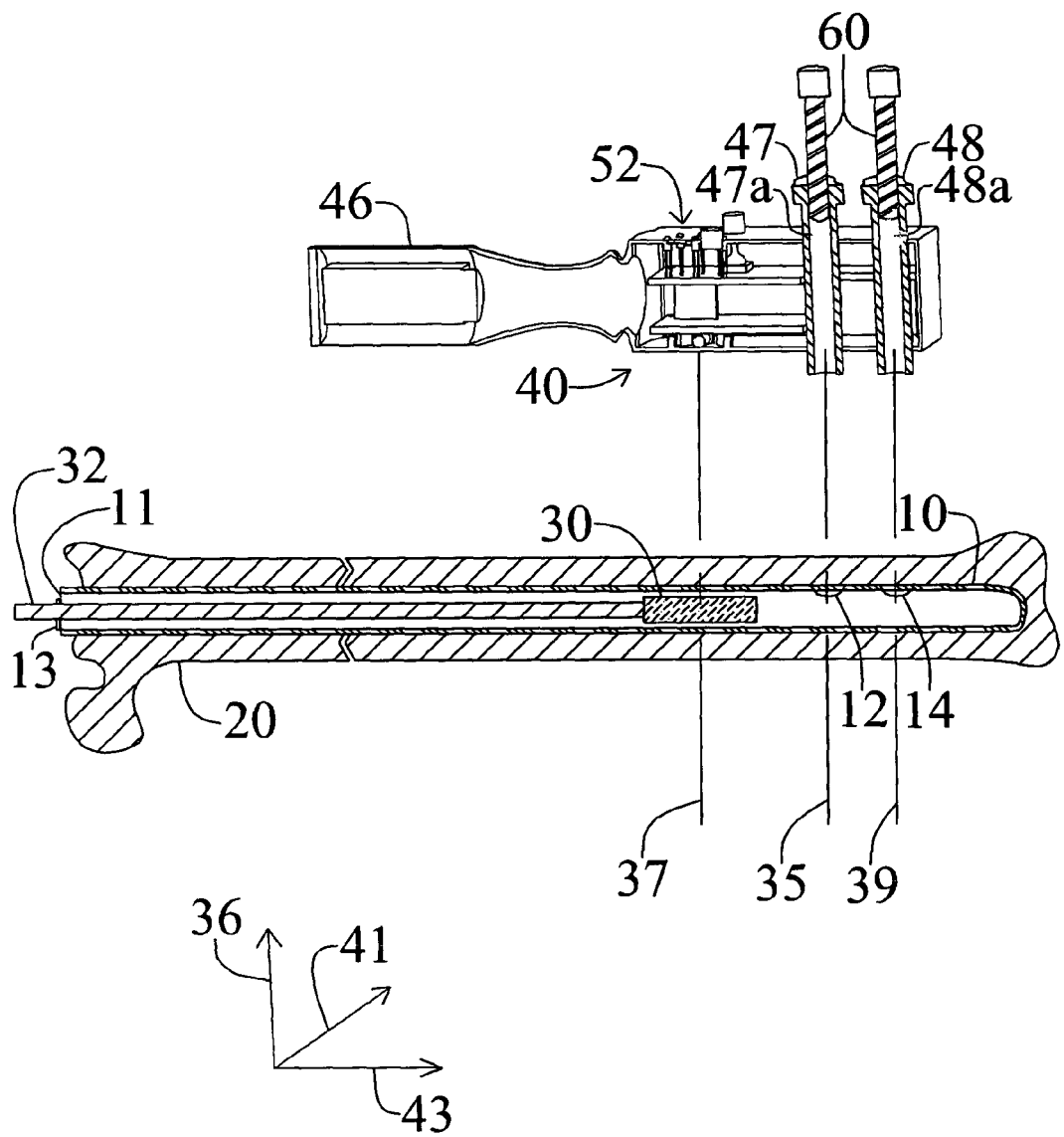
FIG. 7 is a plan view showing the invention in operation.

While the operation of this invention should be self-explanatory from the foregoing description, a brief description of the procedure will now be presented with specific reference to FIG. 7.

The magnet 30 provides no useful information unless it is fixed at a desired location to be targeted. In this case, the magnet 30 must be fixed at an exact known distance from the locking screw openings 12, 14. This distance must match exactly the distance between the center of the sensor array 42 and drill sleeves 47, 48 so that when the sensor array 42 is aligned with the magnet 30, the drill sleeves 47, 48 are aligned with the interlocking openings 12, 14. The small size and shape of the preferred magnet 30 allows it to be inserted in the cannula of the IMN 10 and locked at the correct position proximal to the openings 12, 14 for targeting. The preferred magnet 30 has a diameter of 3 mm, which corresponds to the inside diameter of many IMN's, and thus can be attached to the end of a 3 mm reaming rod 32 for insertion.

For proper targeting, the reaming rod 32 and IMN 10 must be adapted to accommodate a mechanism that locks the magnet 30 in place during the drilling procedure. The magnet 30 only remains locked within the IMN 10 during targeting, and can be removed after interlocking is complete. It is possible of course, in special cases, to incorporate the magnet 30 permanently within an IMN 10. For IMNs 10 with an inside diameter larger than 3 mm, the target magnet 30 may need a carriage built around it (not shown) to maintain centering. The rod 32 adapted to position the target magnet 30 must also have provisions to maintain rotational alignment, so that the north pole remains parallel to the axes 35, 39 of the openings 12, 14 and points in the lateral direction.

In order to align a drill bit 60 with the axes 35, 39 of the desired interlocking openings 12, 14 in FIG. 7, the surgeon must have feedback of positioning for rotation and translation in three dimensions. With specific reference to interlocking opening 12, a coordinate axis is used where it is assumed that the axis 35 of the interlocking screw opening 12 is z 36, and the x-y plane 41, 43, normal to the face of the interlocking screw opening 12, is coplanar with the medial plane. This is the direction from which the surgeon will be locating and drilling the hole in the bone 20. The magnet 30 and targeting device 40 containing the sensing array 42 provide feedback for the surgeon to align the drill sleeve 47 within channel 47a so that it is parallel to the axis 35 of the interlocking screw opening 12 for drilling. The same procedure is used for interlocking opening 14.

The magnet 30 is placed inside the IMN 10 at a position generally proximal to the interlocking screw opening 12 to be targeted. Unless the magnet 30 is permanently positioned within the shaft 15 of the IMN 10, the magnet 30 is inserted by the insertion rod 32 through the proximal opening 11 in the IMN 10, while its insertion depth is fixed by a locking pin 13. Once the magnet 30 is placed at a fixed position 34 adjacent the interlocking screw opening 12, a skin incision is marked using the array of magnetic sensors 42 to locate the position of the now-internal magnet 30 which projects central flux lines 50 illustrated in FIG. 2, parallel to the axis of the interlocking screw opening 12.

From outside the extremity in which the IMN 10 is inserted, the targeting will be performed by an array of magnetic sensors 44 held parallel to the medial plane, illustrated in FIG. 1. These sensors 44 are embedded in the handle 46 of the targeting device 40, which also includes the drill sleeves 47 and 48. Acceptable drill sleeves have been developed previously that could be retrofitted to this design. The distance between the center axis 35 of the drill sleeve 47 and the center axis 37 of the magnetic sensor array 42 will be equivalent to the distance between the magnet 30 and the interlocking screw opening 12 inside the IMN 10. When the sensor array 42 is aligned correctly over the magnet 30, the drill sleeve 48 is aligned with the interlocking screw opening 12. The drill sleeves 47, 48 are removable from the handle 46, so that the empty space can be used as a window to mark the skin to indicate the position of the internal target magnet for incision. The drill sleeves 47, 48 can then be replaced and the drill returned to position for the percutaneous procedure. The surgeon can advance the drill bit 60 through the bone 20 without hitting the magnet 30 while maintaining alignment feedback in real time. Advantageously, the magnet 30 is off-axis, meaning that the magnet is not located in the axes 35, 39 of the drill sleeves 47, 48.

The actual locking mechanism 13 is well known and can be retrofitted to the device of the present invention. An example of an acceptable locking mechanism can be found in *Durham and Crickenberger* (1998).

The exterior display 52 of the sensor array 42 on the upper face of the handle 46 of the targeting device 40 will read a "bull's-eye" of LEDs, which indicate the correct position of the sensors 42 directly underneath the display on the underside of the handle 46. The exterior display 52 indicates the position of the sensors 44 in relation to the target magnet 30. The display 52 will consist of a ring of lights 54, with one offsetting light 56 in the center. The lights 54 light to indicate which position the sensor array 42 must move to correctly align with the magnet 30. When aligned correctly, all lights 54 will be off and the central light 56 will be lit. The drill sleeves 47, 48 will then be aligned with the interlocking transverse screw openings 12 and 14. The surgeon is then ready to drill the holes and insert the interlocking screws without aid of fluoroscopy or extraneous targeting systems.

Other embodiments and uses of the invention will be apparent to those skilled in the art from consideration of the specification and practice of the invention disclose herein. For example, rather than use the above-described electronics, which presently consists of eight separate instrumentation amplifiers, a microcontroller and a handful of resistors and capacitors, the function of the microcontroller and instrumentation amplifiers could be integrated into a single mixed-signal microchip.

The present invention is adaptable to other medical uses, such as tracking and positioning of medical instruments, including endoscopes, catheters and implants within the body. In addition, the present invention can be adapted for use outside the medical industry for locating and targeting areas in materials that are X-ray sensitive and other measurement systems used in industry and manufacturing; providing positioning feedback for robotic devices; and, any process requiring blind hole targeting in non ferrous materials including, precise positioning of opposing elements such as in cabinetry making, fiberglass fabrication and construction and processes involving ceramic and tile fabrication and installation. In embodiments not involving a living body, electromagnets may be used.

All references cited herein for any reason, including all U.S. and foreign patents and patent applications, are specifically and entirely incorporated by reference. It is understood that the invention is not confined to the particular construction and arrangement of parts herein illustrated and described, but embraces such modified forms thereof as come within the scope of the claims following the Bibliography.

BIBLIOGRAPHY OF CITATIONS

1) Durham, A. A. and Crickenberger, D. P. (1998) Magnetic Distal Targeting for Modular Intramedullary Nails. *Techniques in Orthopaedics* 13, 71-78.
2) Krettek, C., Konemann, B., Mannss, J., Schandelmaier, P., Schmidt, U., and Tscherne, H. (1996) [Analysis of implantation-induced nail deformation and roentgen morphometric studies as the principle for an aiming device for distal interlocking nailing without roentgen image intensification]. *Unfallchirurg* 99, 671-678.
3) Krettek, C., Konemann, B., Miclau, T., Schlandermaier, P., and Blauth, M. (1997) In vitro and in vivo radiomorphic analyses of distal screw hole position of the solid tibial nail following insertion. *Clinical Biomechanics* 12, 198-200.
4) Krettek, C., Konemann, B., Miclau, T., Kolbli, R., Machreich, T., Kromm, A., and Tscherne, H. (1998) A new mechanical aiming device for the placement of distal interlocking screws in femoral nails. *Arch Orthop. Trauma Surg* 117, 147-152.
5) Krettek, C., Mannss, J., Miclau, T., Schandelmaier, P., Linnemann, I., and Tscherne, H. (1998) Deformation of femoral nails with intramedullary insertion. *J. Orthop. Res.* 16, 572-575.
6) *Semiconductor Sensors Data Handbook SC*17, Philips Electronics, September 2000
7) Zacheja, J., Bach, T., and Clasbrummel, B. (2000) Application of Microsensors for Minimally Invasive Vascular Flow Measurements and Fracture Repair Systems., Hanover, Germany.
8) U.S. Pat. No. 4,621,628 to Brudermann
9) U.S. Pat. No. 5,049,151 to Durham et al.
10) U.S. Pat. No. 5,514,145 to Durham et al.
11) U.S. Pat. No. 5,703,375 to Durham et al.
12) U.S. Pat. No. 6,162,228, to Durham
13) U.S. Pat. No. 6,503,249 to Krause

What is claimed is:

1. A targeting device for detecting a location and position within a hollow object having an opening, the device comprising:
    a. a magnet adapted to be positioned within the opening of the hollow object, the magnet providing a magnetic field having a shape comprised of a directional field and having a three-dimensional orientation on an x-axis, a y-axis and a z-axis;
    b. a target including a sensor for sensing three-dimensional rotational orientation of the magnet and two-dimensional translational position of the magnet, wherein the sensor comprises an array of sensors dimensioned and configured to detect the x-axis, the y-axis, and the z-axis, and wherein the array is configured to correspond to the magnetic field shape such that each sensor in the array is excited by a same magnitude and a same angle of flux when centered about the z-axis of the magnet; and
    c. a display for displaying alignment of the sensor with the magnet.

2. The targeting device of claim 1 wherein the magnetic field is of sufficient strength to be sensed by the sensor of the target.

3. The targeting device of claim 2 wherein the magnetic field is non-uniform.

4. The targeting device of claim 3 wherein the magnetic field is non-circular, thereby allowing the sensor to distinguish rotation about the z-axis, and recognize magnetic flux lines perpendicular from the magnet which indicate the position of the magnet.

5. The targeting device of claim 1 wherein the magnet is cylindrical in shape.

6. The targeting device of claim 1 wherein the magnet has a diameter less than about 4 mm.

7. The targeting device of claim 1 wherein the magnet is a Neodymium Iron Boron (NdFeB) magnet polarized perpendicular to its long axis.

8. The targeting device of claim 1 wherein the display is a readable display.

9. The targeting device of claim 8 wherein the readable display comprises several Light Emitting Diodes (LEDs), each LED being activated and/or inactivated as the sensors align with the magnet.

10. The targeting device of claim 1 wherein the sensor comprises an elliptical array of four pairs of sensors.

11. The targeting device of claim 10 wherein the sensors sense different outputs between the sensors relative to different spatial positions of each sensor from the magnet.

12. The targeting device of claim 1 further comprising at least one drill sleeve for receiving and aligning a drill bit on an interlocking transverse screw hole in the hollow object.

13. The targeting device of claim 1 wherein the array of sensors comprises aligned, opposing pair members.

14. A targeting device for percutaneously detecting screw openings within an intramedullary nail for internal fixation of long bones, wherein the intramedullary nail has a longitudinal opening and screw holes, the targeting device comprising:

a. a magnet adapted to be positioned within the longitudinal opening of the intramedullary nail, the magnet providing a magnetic field having a shape comprised of a directional field and having a three-dimensional orientation on an x-axis, a y-axis and a z-axis;

b. a target comprising a sensor for sensing three-dimensional rotational orientation of the magnet and two-dimensional translational position of the magnet, wherein the sensor comprises an array of sensors dimensioned and configured to detect the x-axis, the y-axis, and the z-axis, wherein the array is configured to correspond to the magnetic field shape such that each sensor in the array is excited by a same magnitude and a same angle of flux when centered about the z-axis of the magnet, wherein the array of sensors comprises aligned, opposing pair members, and wherein a first distance between members of a first pair of opposing pair members differs from a second distance between members of a second pair of opposing pair members; and c. a display for displaying alignment of the sensor with the magnet.

15. The targeting device of claim 14 further comprising at least one drill sleeve for receiving and aligning a drill bit on an interlocking transverse screw hole within the intramedullary nail.

16. The targeting device of claim 15 comprising a handle holding the sensor and the drill sleeve.

17. The targeting device of claim 14 further comprising two drill sleeves for receiving and aligning a drill bit on the screw holes of the intramedullary nail.

18. The targeting device of claim 17 comprising a handle holding the sensor and the drill sleeves.

19. The targeting device of claim 14 wherein the magnet is fixedly positioned within the opening of the intramedullary nail at a discrete position adjacent to the transverse interlocking screw hole.

20. The targeting device of claim 14 wherein the magnet is positioned on an insertion rod for positioning within the intramedullary nail to a discrete position proximal to the screw holes.

21. The targeting device of claim 14 wherein the magnet generates a flux field sufficient to be sensed by the sensor of the target device.

22. The targeting device of claim 14 wherein the magnetic field is non-uniform.

23. The targeting device of claim 14, wherein the directional field is sensed by the sensor at a distance of about 10 cm.

24. The targeting device of claim 14, wherein the magnet is cylindrical in shape with a diameter of less than about 4 mm.

25. The targeting device of claim 14 wherein the magnet is a cylindrical Neodymium Iron Boron (NdFeB) magnet polarized perpendicular to its long axis.

26. The targeting device of claim 14 wherein the sensor detects the magnet's magnetic flux lines.

27. The targeting device of claim 14 wherein the display is a readable display.

28. The targeting device of claim 14 wherein the display comprises a readable LED display for displaying the sensors in relation to the magnet.

29. The targeting device of claim 28 wherein the readable LED display comprises several LEDs, each LED being activated and/or inactivated as the sensors align with the magnet.

30. A method for detecting a precise location and position within a hollow object having an opening, the method comprising:

a. inserting and positioning a magnet in the opening of the object at a discrete position in the object, wherein the magnet provides a magnetic field having a shape comprised of a directional field and a three-dimensional orientation on an x-axis, a y-axis and a z-axis;

b. providing a targeting device on the discrete position of the magnet, wherein the targeting device comprises a sensor for sensing three-dimensional rotational orientation of the magnet and two-dimensional translational position of the magnet, wherein the sensor comprises an array of sensors dimensioned and configured to detect the x-axis, the y-axis, and the z-axis, wherein the array is configured to correspond to the magnetic field shape such that each sensor in the array is excited by a same magnitude and a same angle of flux when centered about the z-axis of the magnet, and wherein the targeting device further comprises a display for displaying alignment of the sensor with the magnet; and c. moving the targeting device along the object until the sensor aligns with the magnet.

31. The method of claim 30, comprising aligning at least one drill sleeve of the targeting device at a discrete position on the external surface of the object, the drill sleeve having an axis for alignment.

32. The method of claim 30, wherein the magnet provides a non-uniform magnetic field.

33. The method of claim 30, wherein the magnet provides a non-circular magnetic field, thereby allowing the sensor to distinguish rotation about the z-axis, and recognize magnetic flux lines perpendicular from the magnet which indicate the position of the magnet.

34. The method of claim 30, wherein the magnetic flux lines of the magnet are displayed on a readable display.

35. The method of claim 30, wherein the sensors sense different outputs between the sensors relative to different spatial positions of each sensor from the target magnet.

36. The method of claim 30, wherein the sensor in relation to the magnet is displayed on a readable display.

37. The method of claim 36 wherein the readable display comprises several LEDs, each LED being activated and/or inactivated as the sensors align with the magnet.

38. The method of claim 30 for internal fixation of long bones, wherein the hollow object is an intramedullary nail, the intramedullary nail having a longitudinal opening and screw holes.

39. The method of claim 30 wherein the array of sensors comprises aligned, opposing pair members.

40. A method for detecting interlocking screw holes within an intramedullary nail, wherein the intramedullary nail includes a longitudinal opening and an interlocking screw hole, the method comprising:

a. inserting and positioning a magnet having a three-dimensional orientation in the longitudinal opening of the intramedullary nail to a discrete position proximal to the interlocking screw hole, wherein the magnet provides a magnetic field having a shape comprised of a directional field and a three-dimensional orientation on an x-axis, a y-axis, and a z-axis;

b. providing a targeting device to the intramedullary nail, wherein the targeting device comprises a sensor for sensing three-dimensional rotational orientation of the magnet and two-dimensional translational position of the magnet, wherein the sensor comprises an array of sensors dimensioned and configured to detect the x-axis, the y-axis, and the z-axis, wherein the array is configured to correspond to the magnetic field shape such that each sensor in the array is excited by a same magnitude and a same angle of flux when centered about the z-axis of the magnet, wherein the array of sensors comprises aligned, opposing pair members, wherein a first distance between members of a first pair of opposing pair members differs from a second distance between members of a second pair of opposing pair members, and wherein the targeting device further comprises a display for displaying alignment of the sensor with the magnet; and c. moving the targeting device along the intramedullary nail until the sensor aligns with the magnet.

41. The method of claim 40 comprising aligning at least one drill sleeve of the targeting device at a position on the intramedullary nail, the drill sleeve having an axis for alignment.

42. The method of claim 40 comprising aligning the sensor with the magnet and screw openings while simultaneously and in real time monitoring position of a drill sleeve in relation to the interlocking screw hole.

43. The method of claim 40 comprising advancing a drill bit through at least one drill sleeve while maintaining alignment in real time.

44. The method of claim 40 comprising attaching the magnet to an insertion rod.

45. The method of claim 44 comprising inserting the insertion rod into the opening of the intramedullary nail in a specified orientation to a locking point at a most distal interlocking screw hole.

46. The method of claim 40 comprising placing the magnet in the intramedullary nail at a point proximal to the interlocking screw hole.

47. The method of claim 40 comprising fixing the position of the magnet with a locking pin.

48. The method of claim 40 comprising applying the targeting device percutaneously to the approximate region of the interlocking screw hole.

49. The method of claim 40 comprising detecting magnetic flux lines of the magnet to identify a position of the magnet location.

50. The method of claim 40 wherein the interlocking screw hole is a transverse interlocking screw hole.

* * * * *

UNITED STATES PATENT AND TRADEMARK OFFICE
CERTIFICATE OF CORRECTION

PATENT NO. : 7,753,913 B2 Page 1 of 1
APPLICATION NO. : 10/679166
DATED : July 13, 2010
INVENTOR(S) : David C. Szakelyhidi, Jr. et al.

It is certified that error appears in the above-identified patent and that said Letters Patent is hereby corrected as shown below:

On the Title Page, Item (73) Assignee should read: Virginia Tech Intellectual Properties, Inc.
Blacksburg, Virginia (US)

Signed and Sealed this

Nineteenth Day of October, 2010

David J. Kappos
*Director of the United States Patent and Trademark Office*